(12) United States Patent
Heinz-Erian et al.

(10) Patent No.: US 11,674,923 B2
(45) Date of Patent: Jun. 13, 2023

(54) MEANS FOR THE QUANTITATIVE DETERMINATION OF SODIUM CONCENTRATION AND CREATININE CONCENTRATION

(71) Applicants: UNIVERSITÄT INNSBRUCK, Innsbruck (AT); MEDIZINISCHE UNIVERSITÄT INNSBRUCK, Innsbruck (AT)

(72) Inventors: Peter Heinz-Erian, Innsbruck (AT); Gerda Laura Fuhrmann, Axams (AT)

(73) Assignees: UNIVERSITÄT INNSBRUCK, Innsbruck (AT); MEDIZINISCHE UNIVERSITÄT INNSBRUCK, Innsbruck (AT)

( * ) Notice: Subject to any disclaimer, the term of this patent is extended or adjusted under 35 U.S.C. 154(b) by 598 days.

(21) Appl. No.: 16/603,441

(22) PCT Filed: Mar. 20, 2018

(86) PCT No.: PCT/EP2018/056965
§ 371 (c)(1),
(2) Date: Oct. 7, 2019

(87) PCT Pub. No.: WO2018/188909
PCT Pub. Date: Oct. 18, 2018

(65) Prior Publication Data
US 2020/0309726 A1    Oct. 1, 2020

(30) Foreign Application Priority Data
Apr. 12, 2017  (EP) .................................... 17166332

(51) Int. Cl.
*G01N 27/333*  (2006.01)
*A61B 10/00*  (2006.01)
(Continued)

(52) U.S. Cl.
CPC ......... *G01N 27/333* (2013.01); *A61B 10/007* (2013.01); *G01N 27/3275* (2013.01); *G01N 33/70* (2013.01)

(58) Field of Classification Search
CPC ............. G01N 27/333; G01N 27/3275; G01N 27/327; G01N 33/493; G01N 33/5438; G01N 33/70; A61B 10/007
See application file for complete search history.

(56) References Cited

U.S. PATENT DOCUMENTS

| 4,713,165 A | 12/1987 | Conover et al. |
| 2003/0209451 A1* | 11/2003 | Dineen ................ G01N 33/492 205/792 |

FOREIGN PATENT DOCUMENTS

| WO | WO 87/00168 | * 8/1987 |
| WO | 2016/116175 A1 | 7/2016 |

OTHER PUBLICATIONS

J.M.C.S. Magalhaes, et al., "Array of potentiometric sensors for the analysis of creatinine in urine samples", The Analyst, 127(8): p. 1069-1075 (Year: 2002).*

(Continued)

*Primary Examiner* — J. Christopher Ball
(74) *Attorney, Agent, or Firm* — Saliwanchik, Lloyd & Eisenschenk

(57) ABSTRACT

The present invention relates to a single-use test-strip for the quantitative determination of sodium concentration and creatinine concentration and for the subsequent determination of their ratio, and to a non-invasive point-of-care (POC) device for detecting sodium depletion and/or sodium overload in a patient's body. Furthermore, the present invention relates to a method for simultaneously and quantitatively determining sodium concentration and creatinine concentration in a patient's urine sample and to a method of detecting (Continued)

sodium depletion and/or sodium overload in a patient's body.

14 Claims, 10 Drawing Sheets

(51) Int. Cl.
   *G01N 27/327* (2006.01)
   *G01N 33/70* (2006.01)

(56) References Cited

OTHER PUBLICATIONS

Coates, Alison et al. "Evaluation of salt supplementation in CF infants," Journal of Cystic Fibrosis, vol. 8, No. 6, pp. 382-385, Dec. 1, 2009.

Elimosallamy, M.A.F. "New potentiometric sensors for creatinine," Analytics Chimica Acta, Elsevier, Amsterdam, NL, vol. 564, No. 2, pp. 253-257, Apr. 6, 2006.

Guinovart, Tomas et al. "Characterization of a new ionophore-based ion-selective electrode for the potentiometric determination of creatinine in urine," Biosensors and Bioelectronics, vol. 87, pp. 587-592, Aug. 10, 2016.

Heinz-Erian, P. et al. "Decreased Urinary Sodium-to-urinary Creatinine Ratio Identifies Sodium Depletion in Pediatric Acute Gastroenteritis," Klinische Paediatrie, vol. 228, No. 01, pp. 24-28, Jan. 14, 2016.

Phillips, Feyisayo et al. "Measurement of sodium ion concentration in undiluted urine with cation-selective polymeric membrane electrodes after the removal of interfering compounds" Talanta, Elsevier, Amsterdam, NL, vol. 74, No. 2, p. 255-264, Nov. 15, 2007.

\* cited by examiner

MEANS FOR THE QUANTITATIVE DETERMINATION OF SODIUM CONCENTRATION AND CREATININE CONCENTRATION

CROSS REFERENCE TO RELATED APPLICATIONS

This application is a National Stage Application of International Application Number PCT/EP2018/056965, filed Mar. 20, 2018; which claims priority to European Patent Application No. 17166332.1, filed Apr. 12, 2017.

The present invention relates to a single-use test-strip for the quantitative determination of sodium concentration and creatinine concentration and for the subsequent determination of their ratio, and to a non-invasive point-of-care (POC) device for detecting sodium depletion and/or sodium overload in a patient's body. Furthermore, the present invention relates to a method for simultaneously and quantitatively determining sodium concentration and creatinine concentration in a patient's urine sample and to a method of detecting sodium depletion and/or sodium overload in a patient's body.

BACKGROUND OF INVENTION

Sodium depletion (NaD) is a disorder of sodium and fluid balance which is characterized by a pathological decrease of body sodium due to low intake or increased loss of Na (1-3). NaD is routinely diagnosed by finding plasma Na concentrations below the specific reference range. However, and even more alarming, NaD may also be present with normal plasma Na concentrations (4), in particular when patients suffer from proportionate losses of body Na and fluid. This so-called normonatremic Na depletion (NNaD) may occur in case of diarrhea (5), gastrointestinal stoma, acute bleeding, cystic fibrosis (6, 7), burns or intense physical exercise (4). Na depletion (NaD and NNaD) may cause common non-specific symptoms such as sleeping disorders (4), fatigue, headache, confusion, low appetite (3, 8) or growth failure (6, 7, 9) but may also lead to severe complications such as muscle cramps, epilepsy, encephalopathy, coma and even death (10-12). An additional risk for affected patients is that NaD/NNaD is frequently not taken into consideration as a factor causing this symptomatology during the usual diagnostic workup for this symptomatology. Timely identification of NaD/NNaD patients is therefore urgently needed.

Contrary to NaD/NNaD, sodium overload (NaO) is well known to patients and doctors as an important cause of arterial hypertension and its sequelae such as cardiac insufficiency and stroke. However, monitoring of salt status by documenting dietary salt intake and/or Na-excretion in 24-hour urine collections is cumbersome and error-prone and therefore demanding a more simple method of monitoring salt status.

Recently, calculation of the ratio of urinary-sodium-to-urinary-creatinine (uNa/uCr) has been shown to be an excellent marker and promising diagnostic tool for identifying and monitoring patients at risk for NaD/NNaD (5-7). Nevertheless, the determination of uNa/uCr, as is presently performed, is hampered by the need for sending the urine specimen to a laboratory that measures the concentrations of Na using biochemical (13, 14) or conventional electrophysiological methodology (14), and of creatinine by one of the established methods such as capillary electrophoresis or photometry (15). All these methods are performed in centralized medical laboratories, require time and skilled personnel and are not well suited for point-of care (POC) diagnostics.

With the advent of electrochemical device miniaturization enabled by advanced technologies, such as screen printing or inkjet, and maturation of mobile technology, a new era of POC-testing has emerged (16,17,22-24) potentially allowing the quantitative measurement of a variety of analytes as has been demonstrated for glucose in patients with diabetes mellitus.

The probably most accurate way of deter lining body sodium status may be the measurement of tissue sodium concentration by $^{23}$Na-magnetic resonance studies (27) which, however, is very costly and requires a specialized laboratory. Present routines for assessing sodium status and diagnosing NaD are dominated by measurement of sodium concentration in blood (3, 13). The two major methods currently applied are determinations in plasma and (to a lesser degree, also in urine) by flame photometry and by means of a classical Na-selective electrode (14). For these methods, special instrumentation and trained persons are required.

Na-concentrations in blood are often misleading with regard to "true" body sodium status, due to the fact that they may be influenced by compartmental fluid shifts. Urine Na-concentrations are influenced by urine flow and volume dilution and are therefore often related as normalization factor to creatinine concentrations (25). The present "gold standard" for the assessment of sodium balance is the determination of the fractional excretion of Na (FENa; 6-8, 26), which, however, requires the use of the above described conventional laboratory methods for the measurement of Na—, and creatinine concentrations in plasma and urine. This also applies for the determination of uNa/uCr.

Many of the currently available methods for the assessment of human body sodium status are time consuming, and are not usually performed in many routine laboratories.

The routine determination of creatinine in clinical laboratories is based on the Jaffe reaction or on the use of enzyme creatinine amidohydrolase yielding coloured compounds. It is well known that these colorimetric methods are not free from interferences and analytical problems (18, 19). Highly accurate results on creatinine are provided by isotope dilution gas chromatography-mass spectrometry. This method, however, requires expensive and complex instrumentation and trained persons, thus, it cannot be considered a viable routine method. More recently, with the aim to develop a viable routine method to determine creatinine, a few amperometric biosensors mainly relying on complex combination of three enzymes have been reported (20). On the market now available is the i-STAT® (Abbott, US) a portable clinical analyser that makes use of this three-enzyme system immobilized on single-use pocket sized cartridges (21). However, the analysis is performed with blood samples and requires quite high volumes (>65 µL), thus it is invasive and not adequate for monitoring on a daily routine basis. In addition, due to its complexity, the device is rather heavy for self-transport (650 g) and cost intensive.

Nova® Biomedical Stat Profile Critical Care Xpress (CCX) (22) is a benchtop point-of-care device capable of detecting creatinine with an error of approximately 11.4%, and also other analytes including Na. However, the device as all others, requires blood for analysis, thus, it is invasive. It is not a portable device and is rather expensive, as it is an all-in-one system. Additionally, as discussed above, measuring Na-concentration in blood may be misleading with regard to the assessment of Na status as discussed above.

Considering the above information, clearly a less-invasive and less-expensive means to identify and monitor disorders of sodium status is highly desirable.

Accordingly, it was an object of the present invention to provide for means to simultaneously determine sodium and creatinine concentrations in a patient's urine sample in a straightforward manner and to provide such means which can be easily handled. It was furthermore an object of the present invention to provide for a methodology for determining sodium concentration and creatinine concentration in a patient's urine sample for subsequent determining their ratio and for detecting sodium depletion and/or sodium overload that is time-efficient and can be practiced at the point-of-care (POC). It was furthermore an object of the present invention to provide for a methodology for detecting sodium depletion and/or sodium overload in a patient's body which can be practiced even by untrained persons, such as the patient him/herself. It was furthermore an object of the present invention to provide for means and a methodology for quantitatively determining sodium concentration and creatinine concentration in a patient's urine sample and for determining their ratio and/or to detect sodium depletion and/or sodium overload in a patient's body that is not time consuming and that can be performed as a routine operation.

All these objects are solved by a single-use test-strip for the quantitative determination of sodium concentration and creatinine concentration in a patient's urine sample, said test-strip comprising:
- a substrate which either is electrically insulating or which has an electrically insulating layer applied thereon,
- an electrode assembly applied on said substrate or on said electrically insulating layer, if present, said electrode assembly comprising at least
  - one sodium-selective working electrode;
  - one creatinine-selective working electrode;
  - either one joint reference electrode for both said sodium-selective working electrode and said creatinine-selective working electrode, or a reference electrode for said sodium-selective working electrode and a separate reference electrode for said creatinine-selective working electrode;
  - optionally; one or two neutral electrodes for measuring and eliminating interferences,
    - an interface for electrically connecting said electrode assembly to a read out-meter device.

In one embodiment, such determination occurs by potentiometric measurement(s).

It should be noted that, in accordance with the present invention, the determination of the respective concentrations of sodium and creatinine occurs "in combination". By the term "in combination" it is meant that both analytes' concentrations are determined together in or from one sample. However, this does not imply any particular order of determination: For example such determination may occur simultaneously, in a temporally overlapping manner or sequentially. In one embodiment, the analytes' concentrations are determined concomitantly, which essentially means that they are determined together without any substantial temporal interval between these determinations.

In one embodiment, the test-strip according to the present invention is a separate test-strip; in another embodiment, said test-strip forms part of an array of test-strips, such as may be arranged in a roll or on a disc, wherein, for each measurement, one test-strip may be used at a time.

In one embodiment, said substrate is a planar substrate; in another embodiment, said substrate is a non-planar substrate. For example it may also be in the form of a sheet or rod or tube. In one embodiment, the electrodes of said electrode array are all arranged in a single plane; in another embodiment, said electrodes do not necessarily have to be in a single plane, but may be arranged in different planes at an angle to each other. The only requirement is that the electrodes are arranged within the electrode array such that they can be brought in contact with urine when the test-strip is contacted with a urine sample.

In one embodiment, said working electrodes, said reference electrode(s) and said neutral electrode(s), if present, have been applied on said substrate or on said electrically insulating layer, if present, by a suitable deposition technique, such as printing, sputtering, evaporating, electro-less plating, affixation, gluing or lithography, preferably screen printing or ink jet printing, thus forming an electrode assembly on said substrate or on said electrically insulating layer, and wherein said sodium-selective working electrode comprises a sodium-selective membrane, and said creatinine-selective working electrode comprises a creatinine-selective membrane, and wherein said neutral electrode(s) comprises (comprise) a membrane that is not sodium-selective and not creatinine-selective. The purpose of the neutral electrode(s) is to measure and eliminate interference(s). Depending on the type and nature of the(se) interference(s), however, neutral electrode(s) may be selective for such interference/interfering analyte. In one embodiment, as an example, the neutral electrode(s) is (are) proton-selective and comprise(s) a membrane(s) which is (are) proton-selective. Hence, whilst the neutral electrode(s) is (are) not sodium-selective and not creatinine-selective, they may nevertheless be selective for other entities, e. g. protons, in particular for these other entities that give rise to interferences.

In one embodiment, said substrate is made of a material selected from plastic, ceramic, alumina, paper, cardboard, rubber, textile, carbon-based polymers, such as polypropylene, fluoropolymers, such as teflon, silicon-based substrates, such as glass, quartz, silicon nitride, silicon oxide, silicon based polymers such as polydimethoxysiloxane, semiconducting materials such as elemental silicon, and dielectric materials, preferably selected from organic dielectric materials such as polyimide, polycarbonate, polyvinyl chloride, polystyrene, polyethylene, polypropylene, polyester, polyethylene terephthalate, polyurethane, polyvinylidene fluoride or inorganic dielectric materials such as silicium dioxide, and said electrically insulating layer, if present, is made of a dielectric material, preferably selected from wherein, if said electrically insulating layer is present on said substrate, said electrode assembly is located on said electrically insulating layer. The electrically insulating layer maintains electrical isolation between the electrodes and between possible conductive paths on the substrate, in case that the substrate itself is not made of an electrically insulating material.

In one embodiment, said sodium-selective working electrode comprises a sodium-selective membrane that comprises a sodium-selective carrier in a polymer matrix, and said creatinine-selective membrane comprises a creatinine-selective carrier, preferably a protonated creatinine-selective carrier (named also creatininium-selective carrier) in a polymer matrix.

As used herein, therefore the term "creatinine-selective" is meant to refer to a selectivity for either creatinine in protonated or unprotonated form or for both.

The working electrodes may be made of any conductive material, such as carbon, gold, palladium, silver, platinum, titanium, chromium, iridium, tin, their oxides or derivatives and combinations thereof such as fluorine doped tin oxide (FTO) or indium tin oxide (ITO). In one embodiment, said electrodes have been applied on said substrate or on said electrically insulating layer, if present, by a suitable deposition technique, such as printing, sputtering, evaporating, electro-less plating, affixation, gluing or lithography, preferably screen printing or ink-jet printing. The electrodes may be individually deposited or together.

In one embodiment, the reference electrode(s) preferably is a Ag/AgCl system, but other suitable reference material(s) providing a controlled potential in biological fluids are also possible and envisaged.

In one embodiment, said reference electrode is made from the same material as the working electrodes and has a surface, which surface is coated with a polymeric material comprising Ag/AgCl/KCl to maintain constant potential.

In one embodiment, for a higher potentiometric stability, the reference electrode may be in addition coated with a polymeric material including lipophilic salts, such as an anion and cation exchange materials (e.g. different tetraalkylammonium(s) and tetraphenylborates). These components of high lipophilicity exclude or minimize ion exchange with the sample solution and confer constant potential of reference electrode.

In one embodiment, said electrode assembly further comprises one or two neutral electrodes (NE) for measuring and eliminating interferences, wherein said neutral electrode(s) comprise a membrane comprising a polymeric matrix without any sodium-selective carrier and without any creatinine-selective carrier. Typically said neutral electrode(s) comprise the same or similar polymer matrix as in said sodium-selective membrane and/or creatinine-selective membrane of said working electrodes (WE) but without comprising a sodium-selective and creatinine-selective carrier(s). The advantage associated with such neutral electrodes is, that a system incorporating such neutral electrodes is capable of additionally measuring interferences in the sample arising from other analytes, such as e.g. uric acid or ascorbic acid. Therefore, whilst the neutral electrodes are not selective for sodium and not for creatinine, it should, however, be noted that such neutral electrode(s) may be selective for analytes other than sodium or creatinine, e. g. those analytes or entities that give rise to interference(s). In one embodiment, the neutral electrode(s) may be selective for protons. In another embodiment, the neutral electrode(s) may be selective for uric acid and/or ascorbic acid. Also these neutral electrodes each have an electrical lead, respectively, wherein said electrical lead connects said respective electrode with said interface for electrically connecting said electrode assembly to a readout-meter device. (An embodiment of such electrode assembly including neutral electrodes can be seen in FIG. 2D).

In one embodiment, each of said electrodes in said electrode assembly has an electrical lead, respectively, wherein said electrical lead connects said electrode with said interface for electrically connecting said electrode assembly to a readout-meter device.

In one embodiment, said electrical leads may be made of any suitable conductive material, such as carbon, gold, palladium, silver, platinum, titanium, chromium, iridium, tin, their oxides or derivatives and combinations thereof such as FTO, ITO. In one embodiment, said electrical leads have been applied on said substrate or on said electrically insulating layer, if present, by a suitable deposition technique, such as printing, sputtering, evaporating, electro-less plating, affixation, gluing or lithography, preferably screen printing or ink-jet printing. The electrical leads may be individually deposited or together.

It should be noted that both the form and the positional arrangements of the electrodes on the substrate or on the insulating layer, if present, (e.g. round, oval, square, rectangular) are not critical for achieving usable results from the test-strip. Exemplary possible arrangements may for example be: WE1-WE2-RE, WE1-RE-WE2 or e.g. if a neutral electrode is present, WE1-NE-WE2-RE, WE1-WE2-NE-RE, NE-WE1-WE2-RE etc. (WE=working electrode; RE=reference electrode, NE=neutral electrode).

In one embodiment, said joint reference electrode has a surface larger than the surface of each of said working electrodes, or each of said separate reference electrodes has a surface larger than the surface of each of said working electrodes.

The objects of the invention are also solved by a non-invasive point-of-care (POC) device for detecting sodium depletion and/or sodium overload in a patient's body, said POC device comprising:

a readout-meter-device for the quantitative and selective measurement of sodium and creatinine concentrations in a urine sample and for determining a ratio of sodium-to-creatinine, said readout-meter-device comprising a receiving module for receiving an interface of a single-use test-strip according to the present invention and for establishing electrical contact between said readout-meter-device and an electrode assembly of said single-use test-strip, thus allowing the detection and transmission of electrical signal(s) from said single-use test-strip to said readout-meter-device, wherein said receiving module has electrical connectors for separately contacting each electrode via said interface of said test-strip a multichannel amplifier, preferably having high input resistance, for amplifying electrical signal(s) transmitted from a single-use test-strip according to the present invention a controller including an analog/digital converter and a storage memory, for converting electrical signals received from a single-use test-strip according to the present invention into sodium concentration measurement(s) and creatinine concentration measurement(s) and for subsequently determining a ratio of sodium concentration to creatinine concentration based on said sodium concentration measurements and creatinine concentration measurements an output device for indicating concentration measurements and/or said ratio to a user, preferably a display, and a power supply.

In one embodiment, the output device may also additionally indicate other data, e. g. earlier measurements, it may also have additional functions, such as an alarm if a certain threshold of values is exceeded etc. It may comprise a save/send-function etc.

In one embodiment, said controller, for converting electrical signals received from a single-use test-strip according to the present invention into sodium concentration measurement(s) and creatinine concentration measurement(s), makes use of pre-stored calibration information pre-stored in its storage memory. Such pre-stored calibration information is in respect of each analyte, i.e. sodium and creatinine. The controller additionally makes use of the Nernst equation to thereby determine concentration measurements of the respective analyte. For example, in one embodiment, where the electrode assembly comprises a first working electrode (with a first electrical lead), a joint reference electrode (with a second electrical lead), a second working electrode (with a third electrical lead) and a neutral electrode (with a fourth electrical lead), said controller uses a first electrical signal received via the first electrical connector (lead) and the second electrical connector (lead), a second electrical signal via the second electrical connector (lead) and third electrical connector (lead), and, if a neutral electrode is also present, a third electrical signal via a second electrical connector (lead) and fourth electrical connector (lead), to determine sodium and creatinine concentrations, respectively, and to subsequently calculate a ratio thereof.

In one embodiment, said receiving module is in the form of a slit, recess or well or other suitable form allowing to establish a connection to the interface of said test-strip. In one embodiment, said receiving module may be configured as an edge-connector pair or a pin-and-socket-pair.

In one embodiment the non-invasive point-of-care (POC) device according to the present invention, further comprises
- a single-use test-strip according to the present invention inserted into said receiving module of said readout-meter-device by way of said interface of said single-use test-strip, thus establishing electrical contact between said electrode assembly of said test-strip and said readout-meter device.

In one embodiment, said device further comprises
- a user-interface for operating said device, and/or a memory for storing a plurality of sodium and creatinine concentration measurements and calculated ratios of sodium concentration to creatinine concentration, and/or a connection interface, preferably a USB and/or wireless connection interface, for transferring and/or exchanging data with an external computer or external network.

In a further aspect, the present invention relates to a method for quantitatively determining sodium concentration and creatinine concentration in a patient's urine sample, comprising the steps:
a) providing a urine sample
b) contacting a single-use test-strip according to the present invention with said urine sample and allowing the electrode assembly of said test-strip to be wetted by and come into contact with said urine sample, optionally withdrawing the urine-wetted test-strip from said urine sample
c) connecting said test-strip to a readout-meter-device of a point-of-care (POC) device as defined above, to assemble a point-of-care (POC) device as defined above, wherein said single-use test-strip is inserted into said receiving module of said readout-meter device, thus establishing electrical contact between said electrode assembly of said test-strip and said readout-meter-device,
wherein said connecting of said test strip to said readout-meter device of said point of care in step c) occurs either before or after step b),
d) measuring sodium concentration and creatinine concentration in said urine sample, using said point-of-care (POC) device assembled in step c).

Further the present invention relates to a method of detecting sodium depletion and/or sodium overload in a patient's body, said method comprising the steps:
Performing the method for quantitatively determining sodium concentration and creatinine concentration in a patient's urine sample, as defined above,
determining a ratio of sodium concentration to creatinine concentration using said point-of-care (POC) device
detecting a sodium depletion, if a calculated ratio of sodium concentration to creatinine concentration in said urine sample is <8, and detecting a sodium overload, if a calculated ratio of sodium concentration to creatinine concentration is >50. Typically, and in one embodiment, a ratio between 8 and 50 indicates a normal (i. e. healthy) body sodium balance.

In one embodiment, said sodium depletion is a sodium depletion in the plasma of a patient, or is a normonatremic sodium depletion, wherein, in such normonatremic sodium depletion, the sodium concentration in the plasma of a patient is in a normal healthy range, but the patient suffers from a depleted total body sodium pool, e.g. due to proportional losses of sodium and of fluid in the body, such as may occur in diarrhea, gastrointestinal stoma, acute bleeding, cystic fibrosis, burns or intense physical exercise. For clarification and without wishing to be bound by any theory, normonatremic sodium depletion may occur in the following exemplary scenario: The blood Na concentration is the concentration of Na within only one of the body compartments. Other compartments besides this intravascular compartment of all blood vessels are: intracellular (cells of all tissues) and extracellular (between cells but not within the blood circulation). If Na in one of these compartments is low or if—due to little fluid in the circulation, little fluid and Na perfuse the kidneys, the kidneys retain Na and thus little Na is excreted and the uNa/uCr is low.

The present inventors have provided for a simple, sensitive, non-invasive, quantitative and low-cost portable single-use test-strip for the simultaneous quantitative determination of sodium and creatinine concentrations in a patient's urine sample and for a non-invasive, quantitative, low-cost and portable point-of-care (POC) device for detecting sodium depletion and/or sodium overload in a patient's body. The test-strip and the point-of-care device enables electrochemical measurements of urinary concentrations of sodium and creatinine for the subsequent calculation of their respective ratio (sodium:creatinine) to be used as a marker of sodium depletion (NaD/NNaD) and/or sodium overload (NaO).

It should be noted that the simultaneous quantitative determination of sodium concentration and creatinine concentration occurs in an enzyme-free manner. Hence, no enzymes are used for such determination, and no products of an enzymatic reaction are measured/determined. Such determination is based on potentiometric measurements, i.e. it involves the measurement of differences in electric potential. It does not involve measurements of electric current.

A "test-strip", as used herein, in a simple embodiment, is meant to refer to a substrate that is to be brought in contact with a sample, in order for the quantitative measurement of sodium and creatinine concentrations to be performed. The test-strip may take any form that is suitable to be contacted with a patient's sample, such as a rectangular form, square form, circular form or oval form. In one embodiment, the test-strip is planar, having a planar electrically insulating substrate on which an electrode assembly has been applied. However, in other embodiments, the test strip may also adopt other shapes and forms, such as a sheet or rod or tube, provided such form is suitable to accommodate a substrate on which an electrode array can be deposited. In one embodiment, said substrate is a planar substrate; in another embodiment, said substrate is a non-planar substrate. For example it may also be in the form of a sheet or rod or tube. In one embodiment, the electrodes of said electrode array are all arranged in a single plane on said substrate, or on said insulating layer, if present; in another embodiment, said electrodes do not necessarily have to be in a single plane, but may be arranged in different planes at an angle to each other. The only requirement is that the electrodes are arranged within the electrode array such that they can be brought in contact with urine when the test-strip is contacted with a urine sample.

In one embodiment, the test-strip according to the present invention is a single test-strip, on its own; in another embodiment, said test-strip forms part of an array of test-strips, such as may be arranged in a roll or on a disc, wherein, for each measurement, one test-strip may be used at a time. Hence, the present invention also envisages and relates to a plurality of test-strips in accordance with the present invention which are connected with each other. Hence the present invention also relates to an array of test-strips according to the present invention. In such array, each test-strip is intended for single use, but the entire array may be used for as many times as there are test-strips in such array. In one embodiment, such array of test-strips may be provided in the form of a cartridge or other dispensing device which allows the sequential use of test-strips. In one embodiment, within such array, the test-strips may be releasably connected with each other, such that, for example, if a test-strip is to be used for a measurement, it can be disconnected from the array and be used thereafter.

The term "sodium-selective" and "creatinine-selective", as used herein, in the context of an electrode or a membrane, is meant to refer to an electrode or membrane that is specifically and selectively sensitive for sodium and/or creatinine, respectively. In one embodiment, such specific and selective sensitivity of an electrode is achieved by applying a sodium-selective membrane or a creatinine-selective membrane on said electrode. In one embodiment, such sodium-selective membrane or more generally, analyte-selective membrane is produced by applying an analyte-selective membrane solution onto the surface of the respective electrode. The application may be done by dispensing, drop casting, screen printing, spin coating or any other suitable deposition method. Such an analyte-selective membrane solution typically contains an analyte-specific carrier molecule such as an ionophor. The solution also typically contains a polymer and a solvent. Such solution may also and optionally contain other components, such as plasticizers, and/or a cation-exchanger salt. The analyte-selective solution may be prepared for example by dissolving all components in a suitable solvent. Suitable solvents are manifold, e.g. tetrahydrofurane or dimethylformamide. Once the analyte-selective membrane solution has been applied onto the surface of the electrode, the solvent is removed by drying, evaporation, etc., and what remains is a polymeric membrane which contains analyte-specific and -selective carriers.

Typically, and in one embodiment, sodium-selective carriers are crown ethers, calix(4)arenes, silacrown ethers and related macrocyclic hosts as well as noncyclic di- and tri-amides or derivatives from the monensin (carboxylic acid antibiotics) family. Examples of sodium-selective carriers are 4-tert-butylcalix(4)arenetetraacetic acid tetraethyl ester, 2,3:11,12-didecalino-16-crown-5; bis[(12-crown-4)methyl] dodecylmethylmalonate; bis[(12-crown-4)methyl]2,2-didodecylmalonate; 4-octadecanoyloxymethyl-N,N,N',N'-tetracyclohexyl-1,2-phenylenedioxydiacetamide; (N,N',N''-triheptyl-N,N',N''-trimethyl-4,4',4''-propylidynetris(3-oxabutyramide); N,N'-dibenzyl-N,N'-diphenyl-1,2-phenylenedioxydiacetamide); monensin methyl ester or Monensin docdecyl ester.

In one embodiment, prior to the potentiometric measurement, the creatinine has to be protonated to form a creatininium ion by adjusting the pH of said sample by addition of a suitable buffer. The term "creatinine-selective" is meant to encompass a selectivity for creatinine, irrespective and independent of the protonation state of said creatinine. Hence, a creatinine-selective electrode is selective for either creatinine in non-protonated form or in protonated form or both. In one embodiment, a suitable pH is below 5, and suitable buffers are manifold. e.g. they may be acetate, citrate, or phosphate. Typically, and in one embodiment, protonated creatinine-selective carriers (creatininium-selective carriers) may be selected from the family of crown ethers, $\alpha$-, $\beta$-cyclodextrines, calixpyrroles, amino-pyridone and amino-pyrimidones. Examples of creatinine-selective carriers are dibenzo-30-crown-10; tri-o-octyl-$\beta$-cyclodextrin; 2,6-di-o-dodecyl-$\beta$-cyclodextrin; 1-(5,7,7-trimethyl-2-(1,3,3-trimethylbutyl)-octyl)isocytosine.

In one embodiment, the creatinine-selective carrier may be a crystalline ion-pair complex, such as creatinine tungstophosphate, creatinine molybdophosphate or creatinine picrolonate.

Polymers or mixture of polymers, that may be used for the preparation of the membrane solution (from which a polymer matrix is generated) and which subsequently function as a polymer matrix in the membrane are manifold and, in one embodiment, are selected from polyvinyl chloride, polystyrene, polyacrylates, polycarbonates, polyesters, polyamides, polyurethanes, polyvinylidene chloride, polyvinyl acetate, polyvinyl alcohols, polysiloxanes, polymetacrylates, silicone elastomers, cellulose esters.

Possible are also fluorous phases of these polymers to realize extremely hydrophobic analyte-selective electrode (ASE) membranes, e.g. ion-selective electrode (ISE) membranes.

In one embodiment, the polymers are preferably of high molecular average weight to guarantee an inert character of the membrane.

In one embodiment, the percentage weight of polymeric material is from 20 to 40% in relation to the total weight of the analyte-selective membrane.

In one embodiment, one or several plasticizers are included in the membrane solution. Their role is to make the membrane softer and resistant to mechanical stress. In one embodiment, plasticizer(s) that may be used in the membrane solution, may be selected from o-nitrophenyl-octylether, bis(2-ethylhexyl)adipate, bis(2-ethylhexyl)sebacate, dioctyl sebacate, dioctylphenyl phosphonate, dimethyl phthalate, dibutyl phthalate, dioctyl phthalate, hexamethylphosphoramide, bis(1-butylpentyl)adipate, chloroparaffin. In one embodiment, the plasticizer is present in an amount sufficient to solvate analyte-selective carrier in the polymeric material. In one embodiment, the weight ratio plasticizer to analyte-selective carrier is 10:1 to 100:1. In one embodiment, the weight ratio of plasticizer:polymer in typical plasticizer:polymer mixtures is in a range of from 1:1 to 4:1. In one embodiment, the percentage weight of plasticizer is from 40 to 80% in relation to the total weight of the membrane.

Optionally, and in certain embodiments, in particular when the analyte-selective carrier is a neutral molecule, a cation-exchanger salt may be added in the polymer matrix. In one embodiment, such salt is composed from a large negatively charged organic molecule and a small cation. Its function is to help maintaining permselectivity of the membrane by complementing each cationic analyte captured by the membrane by the large negatively charged organic molecule, e.g. a lipophilic anion, and exchanging in the membrane only ions with the same sign.

Examples for such cation exchanger salts are potassium or sodium tetrakis[3,5-bis(trifluoromethyl)phenyl]borate, potassium or sodium tetrakis(p-chlorophenyl)borate, potassium or sodium tetrakis[3,5-bis(1,1,1,3,3,3-hexafluoro-2-methoxy-2-propyl)phenyl]borate.

In one embodiment, typical molar ratios of cation-exchanger salt:analyte selective carrier mixtures are in a range of from 1:10 to 1:2. In one embodiment, the percentage weight of cation-exchanger salt is from 0.1% to 2% in relation to the total weight of the membrane. It is however, clear that with respect to the polymer matrix and its different components, these different components of the polymer matrix will be present and used in such amounts that their total will be 100% by weight.

Optionally, and in some embodiments, before applying the analyte-selective solution onto the surface of the respective electrode, or a polymeric material comprising Ag/AgCl/KCl or a lipophilic salt, on the reference electrode, an "inner contact layer" material (also called ion-to-electron transducer) may be coated on said electrode. Without wishing to be bound by any theory, such inner contact layer has the function of avoiding the formation of capacitive layers at the electrode/membrane interface. Examples of materials suitable as "inner contact layer" are conducting polymers such as polyaniline, poly(3,4-ethylenedioxythiophene), poly(3-octylthiophene), polypyrrole, polyaniline, conductive carbon based materials such as graphene, carbon nanotubes, graphene, graphene oxide, reduced graphene oxide or metal nanoparticles. In one embodiment, they may be solubilized or dispersed in a suitable solvent and applied onto the surface of the said electrode by dispensing, drop-casting, screen printing, spin coating or any other suitable deposition method. Once the solution/dispersion has been applied onto the surface of the electrode, the solvent is removed by drying, evaporation, etc., and what remains is an "inner contact layer" on which afterwards the analyte-selective membrane is applied.

In one embodiment, the "inner contact layer" material may, optionally, also be directly included in the polymeric membrane solution of the analyte-selective membrane or polymeric material applied on the reference electrode.

In some embodiments, although the electrodes should be in electrical contact with the liquid sample, e.g. urine sample, it may be useful to prevent the electrode array and electrical leads from coming into contact with larger molecules or urinary components, such as proteins, which may interfere with and have a negative impact on the quality of the determination(s) of concentration(s). (Such worsening process, due to larger molecules is called "biofouling"). Therefore, in some embodiments, optionally, a covering membrane may applied on the portion of said test-strip which is intended to come into contact with said urine sample. An example of such a suitable covering membrane is a polycarbonate material, e.g. those sold under the Trade Mark "Nucleopore" allowing the trapping of large interfering molecules.

Furthermore, in some embodiments, at the end of the fabrication of a test-strip, a suitable covering film, e.g. a plastic insulating material having openings for the electrodes can be applied on the test-strip (FIG. 4) to build up a test-strip (2a) having an exposed electrode array 4 and terminal interface 5, for omitting contamination of electrical leads during storage and processing and for the commodity of use for the user.

It should be noted that, in one embodiment, the test-strip in accordance with the present invention is not a rod-like structure, but is or comprises a planar electrically insulating substrate. In one embodiment, the quantitative determination of sodium and creatinine concentrations is not based on colorimetric or amperometric measurements. In one embodiment, it is based on potentiometric measurements. Moreover, in one embodiment, the quantitative determination of sodium and creatinine concentrations according to the present invention does not involve the use of enzymes, nor any oxidation/reduction reaction nor any hydrolysis of an analyte.

In embodiments according to the present invention, the single-use test-strip is to be used in connection with a point-of-care device in accordance with the present invention for detecting sodium depletion and/or sodium overload. For that purpose, the single-use test-strip has a suitable interface for electrically connecting the electrode assembly of said test-strip to a readout-meter-device which forms part of the point-of-care device of the present invention.

Such interface may take any suitable form and may, in one embodiment, be a set of electrical contacts coming from the electrode assembly on the planar substrate. Such interface may, for example, take the form of a plug, with the electrical contacts forming part of said plug. The interface is suitable for electrically connecting the electrode assembly to a readout-meter device of a non-invasive point-of-care device for detecting sodium depletion and/or sodium overload, wherein such point-of-care device comprises a readout-meter-device having a receiving module for receiving an interface of a single-use test-strip according to the present invention, e.g. in the form of a recess or well or slit, for receiving the interface of the test-strip. In one embodiment, such receiving module may take the form of a socket. Typically, the receiving module is suitable to accommodate the interface of the single-use test-strip.

The term "sodium concentration in a urine sample" or "in urine" is herein also sometimes abbreviated as "uNa". The same applies to "creatinine concentration in a urine sample" or "in urine", which is abbreviated as "uCr". The ratio of sodium concentration to creatinine concentration in a urine sample is herein also sometimes abbreviated as "uNa/uCr".

The abbreviation "EMF", as used herein, refers to the electromotive force, which essentially refers to a difference in potential between two electrodes. Such electromotive force is quantitatively related via the Nernst equation to the corresponding analyte concentration in a sample. Typically, the potentiometric signal or measurement that can be taken from a test-strip according to the present invention is an electromotive force which can then be related/converted into an analyte concentration. The abbreviation "WE", as used herein, refers to a working electrode, the abbreviation "RE" refers to a reference electrode, and the abbreviation "NE" to a neutral electrode.

The substrate that is comprised by the test-strip is preferably made of an electrically insulating material. In one embodiment, such electrically insulating material is a dielectric material, such as plastic, ceramic, alumina, paper, cardboard, rubber, textile, carbon-based polymers, such as polypropylene, fluoropolymers, such as teflon, silicon-based substrates, such as glass, quartz, silicon nitride, silicon oxide, silicon based polymers such as polydimethoxysiloxane, semiconducting materials such as elemental silicon. The substrate may optionally be coated with an electrically insulating layer. Such electrically insulating substrate is preferably made of a dielectric material, preferably selected from organic dielectric materials such as polyimide, polycarbonate, polyvinyl chloride, polystyrene, polyethylene, polypropylene, polyester, polyethylene terephthalate, polyurethane, polyvinylidene fluoride or inorganic dielectric materials such as silicium dioxide. In one embodiment, the electrode assembly that is applied on the substrate or on said electrically insulating substrate, if present, is part of and/or forms part of the surface of the substrate and is suitable to be brought in contact with a patient's sample, such as a urine sample. If an electrically insulating layer is present on the substrate, the electrode assembly is preferably located and applied on such electrically insulating layer.

The test-strip, in accordance with embodiments of the present invention is a single-use test-strip, which means that after having been used once for measurements of sodium and creatinine concentrations, it is disposed. Hence, the test-strip in accordance with embodiments of the present invention is a disposable test-strip. It is to be used in conjunction with a non-invasive point-of-care (POC) device in accordance with the present invention for detecting sodium depletion and/or sodium overload in a patient's body. Such point-of-care device comprises a readout-meter-device for the quantitative and selective measurement of sodium and creatinine concentrations in a urine sample and for determining a ratio of sodium-to-creatinine concentration. Such readout-meter-device is suitable and configured to quantitatively measure electrical signals received from the single-use test-strip connected to the readout-meter-device. Furthermore, the readout-meter-device is configured to calculate the concentrations of analytes, namely sodium and creatinine, and their ratio based on the electrical signals and calibration information, and is also configured to output, e.g. display the results to a user. In one embodiment, such readout-meter-device comprises a controller that is configured to measure electrical signal(s) received from said test-strip, and to calculate concentrations based on such electrical signal(s). Furthermore, the readout-meter-device comprises an output device connected to the controller for outputting results for inspection by a user. Furthermore, the readout-meter-device comprises a USB and/or wireless port for exchanging data with an external computer or network.

The single-use-test-strip and the point-of-care (POC) device in accordance with the present invention are low-cost devices and extremely easy to handle and can therefore also be used by non-medical staff and patients. The devices are pocket-type portable, and they can be used in a non-invasive manner and are therefore providing a good basis for optimal patient compliance. This is, for example, particularly advantageous in children because the need for blood-taking is obviated. Furthermore, the devices and the methodology according to the present invention reduce the time as well as the technical and logistic complexity and the cost of routine clinical analysis and thereby greatly facilitate the analysis of body sodium status.

The present invention is now further described by reference to the following figures, wherein FIG. 1 shows a schematic representation of an embodiment of a point-of-care (POC) device for detecting sodium depletion and/or sodium overload in a patient's body; EMF=electromotive force; uNa=sodium concentration in a urine sample; uCr=creatinine concentration in a urine sample; uNa/uCr=ratio sodium:creatinine concentration. 1=POC device, 2=test-strip, 3=readout-meter device, 4=electrode assembly, 5=interface for electrical connection, 6=sodium-selective electrode, 7=creatinine-selective electrode, 8=reference electrode, 9=electrical leads FIG. 2 shows top views of exemplary test strips with exemplary possible patterns of an electrode array and electrical leads applied on an insulating layer A) exemplary round shape of working electrodes+oval reference electrode
5=interface for electrical connection
6=sodium-selective electrode
7=creatinine-selective electrode
8=reference electrode
9=electrical leads
B) exemplary square shape of working electrodes+rectangular reference electrode
C) 9a)=exemplary contact paths at the end of electrical leads for contacting readout-meter device
D) 10=neutral electrode for determining interferences FIG. 3 shows cross-sectional views of an exemplary analyte-selective electrode
A) Without "inner contact layer"
11=substrate
12=insulating layer
13=conductive layer
14=analyte-selective membrane
B) With "Inner contact layer"
11=substrate
12=insulating layer
13=conductive layer
14=analyte-selective membrane
15=optionally, "inner contact layer" (transducer)

FIG. 4 shows an exemplary embodiment for the fabrication of an exemplary test-strip with an additional covering layer. In such exemplary fabrication method, the following steps are performed:
Step 1) Provide substrate with insulating layer on top
Step 2) Apply electrode assembly and electrical leads
Step 3) Form analyte-selective electrodes
Step 4) preferably, apply a suitable covering film, e.g. a plastic insulating material with openings for the electrodes
2a=test-strip with covering layer
4a=electrode assembly and electrical leads
5=interface for electrical connection
11a=substrate with insulating layer
15a=analyte-selective membrane solutions
16=covering film with openings for electrodes FIG. 5 shows the potentiometric response of fabricated test-strips (T1-T4) according to the present invention to different concentrations of sodium in aqueous solutions.

Figure 8:
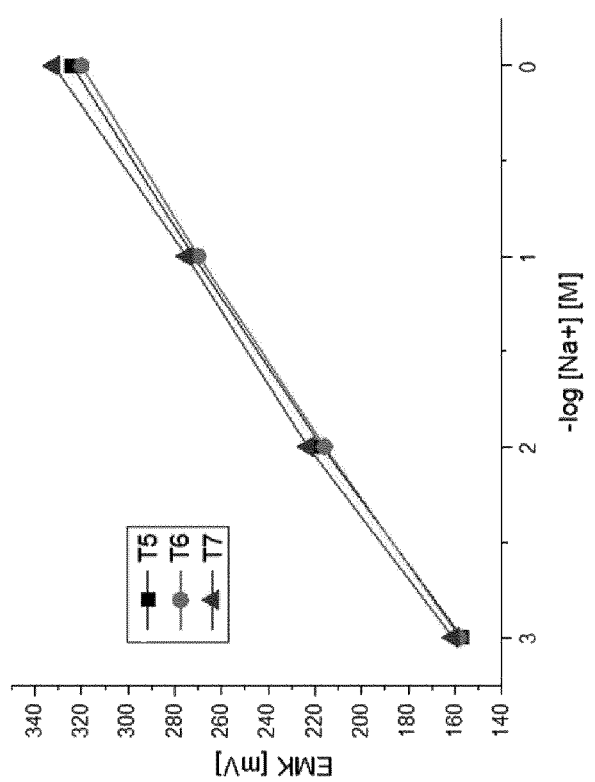
Figure 9:
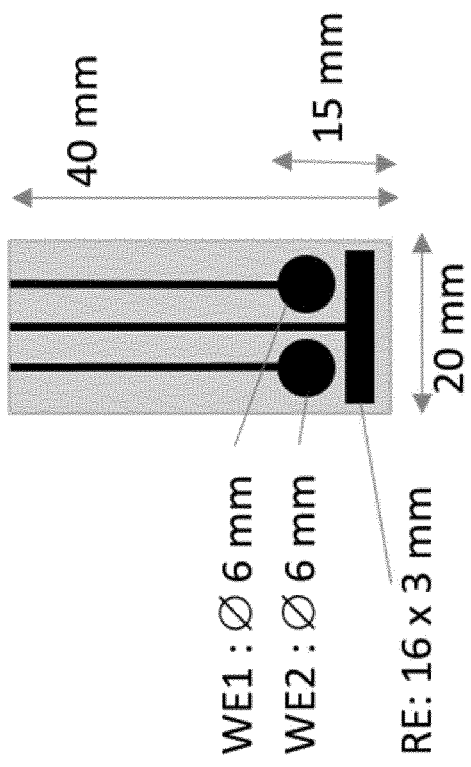

FIG. 8 shows a near-Nernst potentiometric response of exemplary fabricated test-strips in accordance with the present invention (T5-T7) to different sodium concentrations in a 0.5 M calcium chloride aqueous solutions FIG. 9 shows top view of an exemplary test strip with exemplary dimensions of the electrode array and substrate. WE1=a first working electrode; WE2=a second working electrode; RE=reference electrode.

Figure 10:
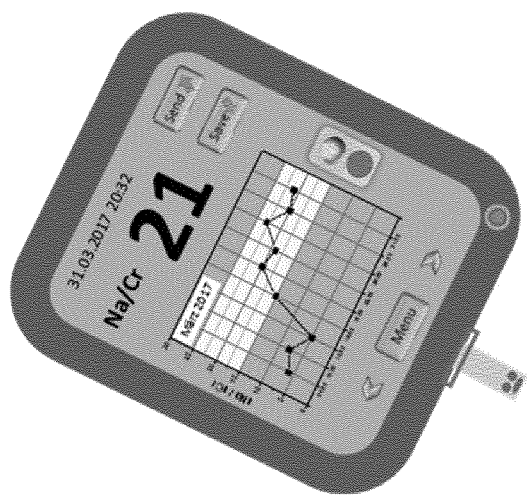

FIG. 10 shows an exemplary point-of-care (POC) device for detecting sodium depletion and/or sodium overload in a patient's body consisting of a test-strip and readout-meter displaying exemplary analysis results.

Furthermore, the present invention is now further described by reference to the following examples which are given to illustrate, not to limit the present invention.

EXAMPLES

Proof of Function for Sodium Specific Test-Strip
Initial proof of function of Na-specific test membranes loaded on commercial Gwent® test-strips was obtained by
- successful potentiometric measurements of Na concentrations in fluids with predetermined Na concentrations and in native human urine samples
- proven linear (dynamic) range of the test strips for relevant concentrations of sodium in physiological fluids
- good agreement of Na-concentrations in human urine with the values measured by conventional methods including AAS and ISE
- proven near-Nernst potentiometric response for relevant concentrations of sodium in physiological fluids Initial proof of function of creatinine-specific test membranes loaded on commercial Gwent® test strips was obtained by
- successful potentiometric measurements of creatinine concentrations in fluids with predetermined creatinine concentrations and human urine

Example 1) Fabrication of Sodium-Selective Test Strips

For proof-of-principle experiments, a commercially available 2-Electrode System (Gwent, UK, BE 2070921D1/007) was used. The system consists of a carbon working electrode (WE) with Ø=6 mm and a common (Ag/AgCl) counter/reference electrode (RE) that are screen printed onto a 12.0×26.5 mm plastic substrate.

To realize a sodium selective electrode (Na-ISE), an ion selective membrane (Na-ISM) solution (30 µL) was casted on the area of the carbon WE. Then, the substrate was dried to remove solvent. The Na-ISM solution consisted of a mixture of 4.0 mg sodium ionophore X (4-tert-butylcalix[4]arenetetraacetic acid tetraethyl ester), 1.0 mg KTpClPB (potassium tetrakis(4-chlorophenyl)borate), 133 mg PVC (high molecular weight polyvinylchloride) and 266 mg o-NPOE (2-nitrophenyl octyl ether) in 3 mL tetrahydrofuran.

Example 2) Potentiometric Measurements with a Sodium Selective Test Strip

Prior to measurement, for conditioning the Na-ISE electrode, the test strip was immersed overnight into a sodium chloride solution (1M aq. NaCl). The substrate with both electrodes was introduced into the sample solution and the potential difference (EMF) between modified WE (Na-ISE) and RE was measured with a simple digital voltmeter.

Example 3) Sensor Calibration by Measuring a Standard Sodium Solution Series Standard solutions with sodium concentrations of 1M, $10^{-1}$M, $10^{-2}$M, respectively, were prepared by dissolving sodium chloride (NaCl) in water. The EMF values were recorded and a calibration curve was set up by plotting the EMF values as a function of the minus logarithm of sodium concentrations. Four different test strips (T1-T4) were fabricated and tested. The results are summarized in Table 1.

TABLE 1

EMF values for three different $Na^+$ concentrations (1.0-0.01M) obtained by measurements with four different test strips (T1-T4)

| c(Na+) [M] | EMK [mV] T1 | EMK [mV] T2 | EMK [mV] T3 | EMK [mV] T4 |
|---|---|---|---|---|
| 1 | −118 | −114 | −119 | −119 |
| 0.1 | −25 | −23 | −19 | −21 |
| 0.01 | 60 | 64 | 65 | 63 |

Figure 1:
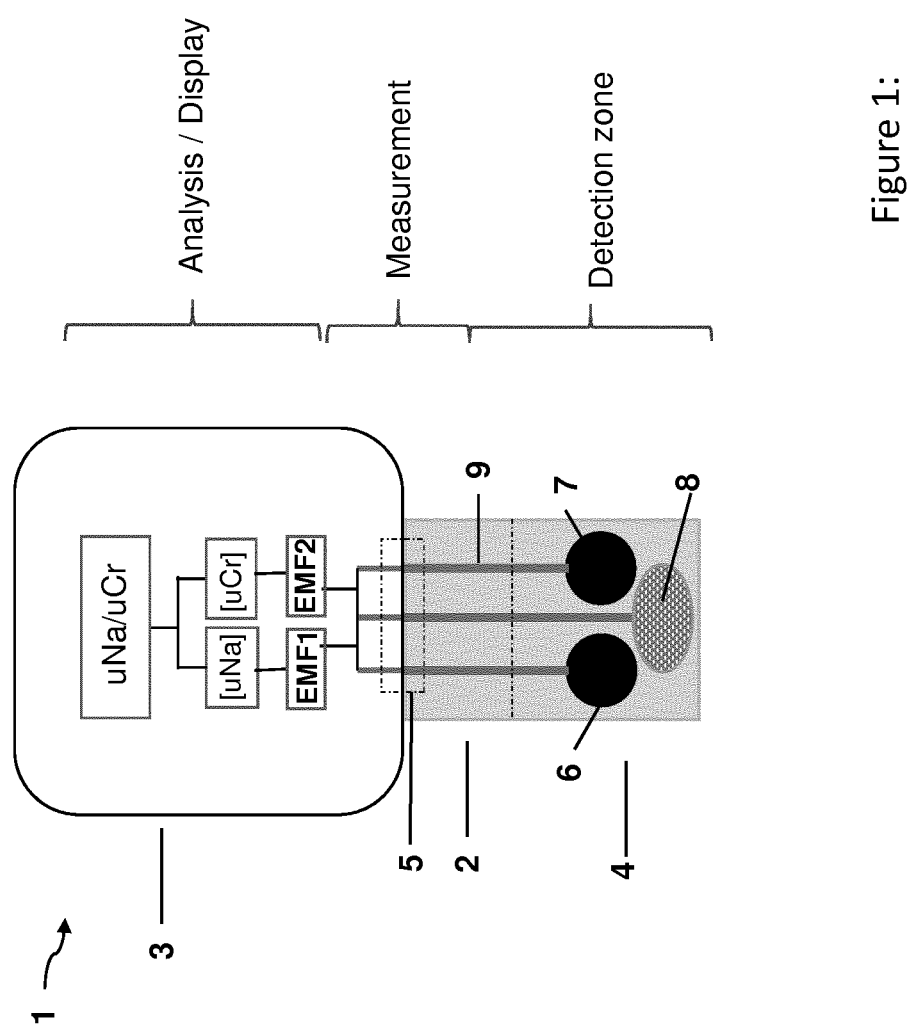
Figure 2:
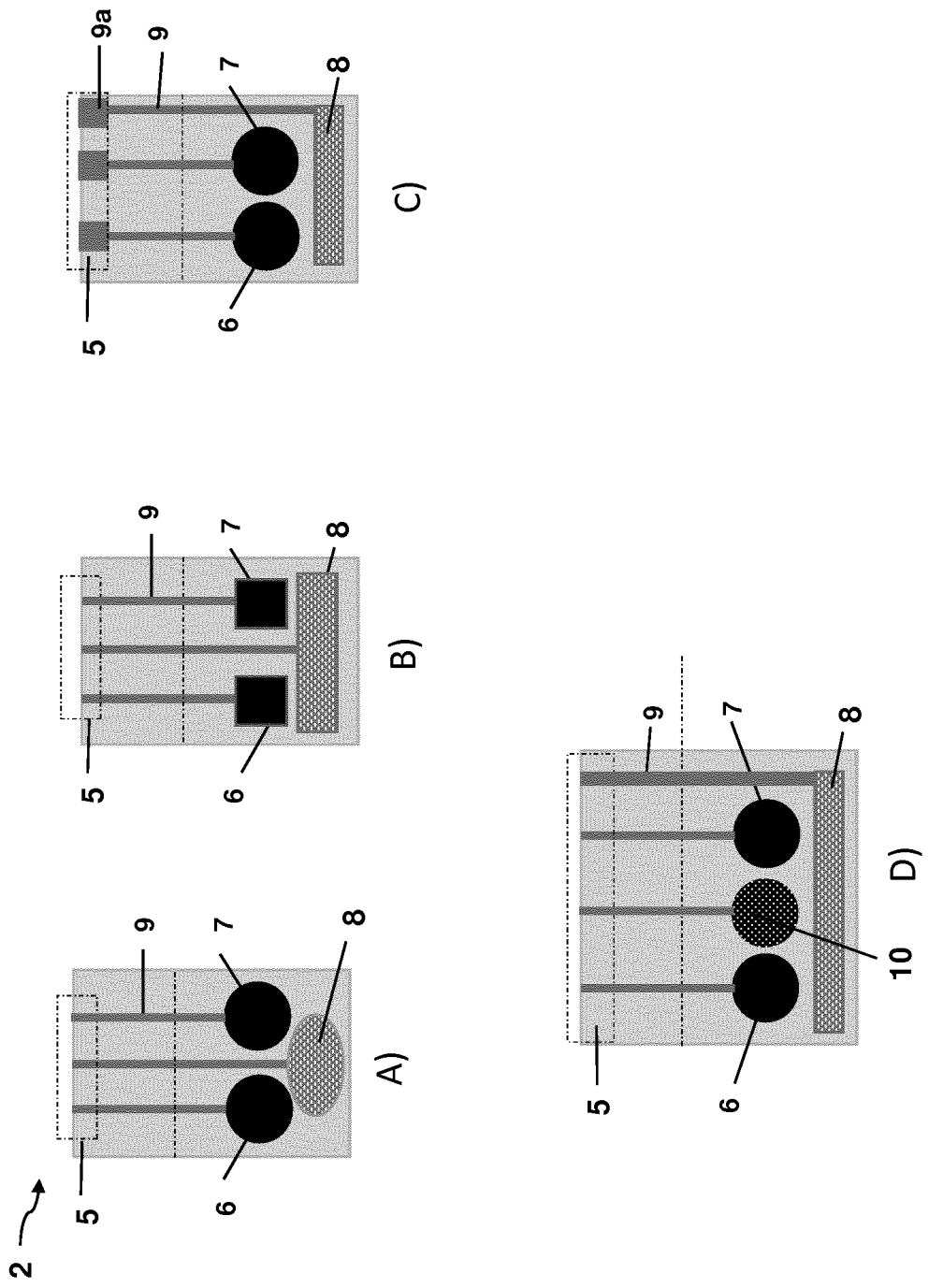
Figure 3:
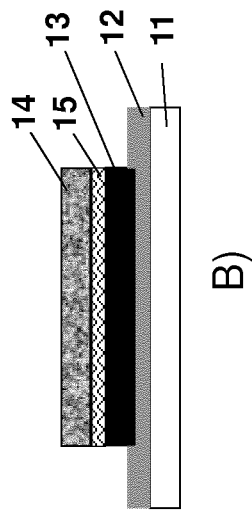
Figure 3:
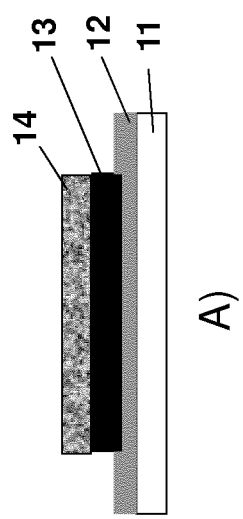
Figure 4:
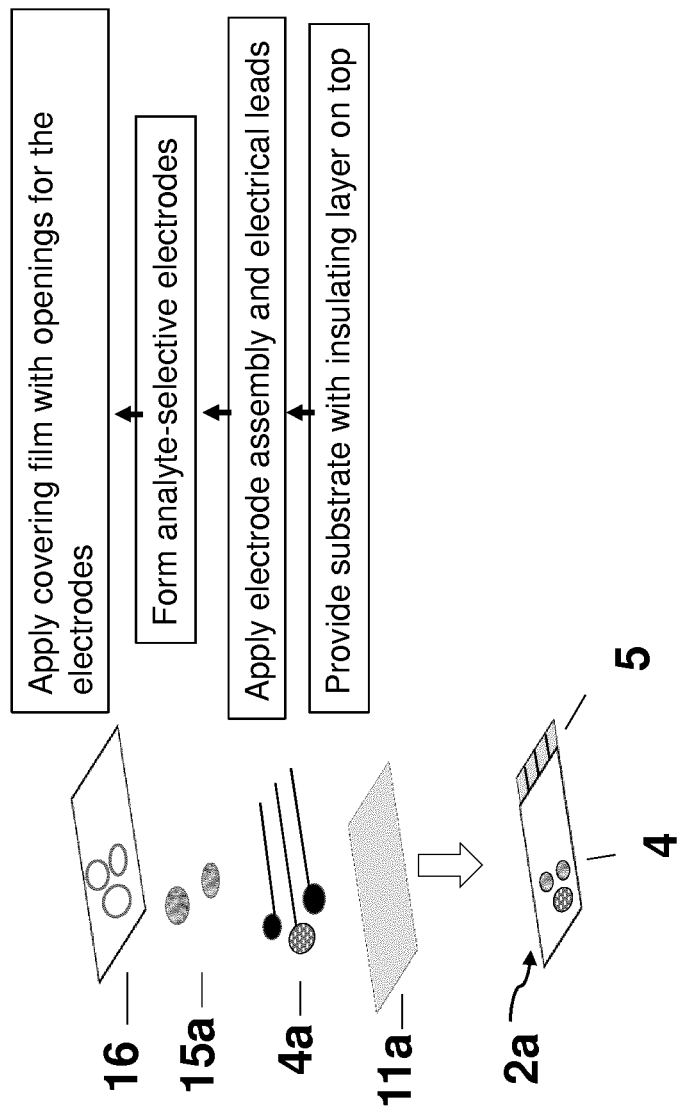
Figure 5:
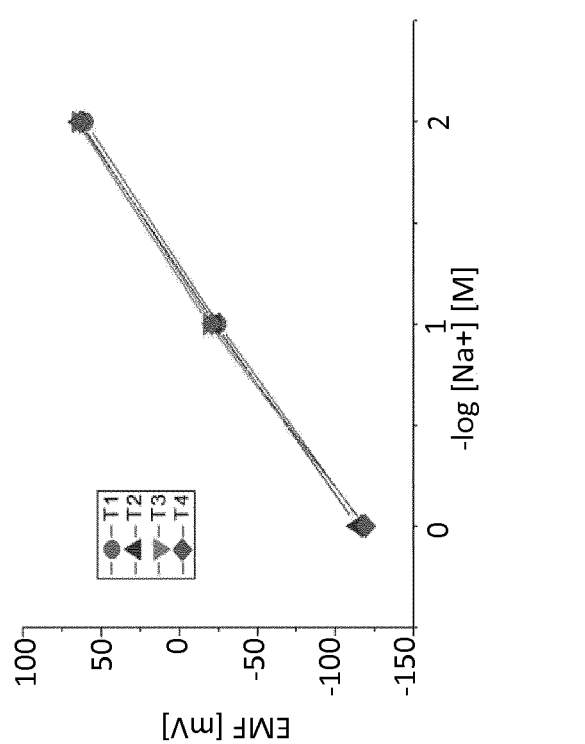

The data clearly show good reproducibility and—as shown in FIG. 5—a linear (dynamic) range between 0.01 and 1 M sodium solution. Thus, the linear range of the test strips covers medically relevant concentrations in physiological fluids, as in human urine where the normal range for Na concentrations lies between 0.02-0.25 M.

Out of these data for each test strip a regression equation with the corresponding correlation coefficient R, was calculated (Table 2).

TABLE 2

Overview of linear regression equations and correlation coefficients obtained for EMF measurements with four different sodium sensors (T1-T4)

| Sensor | Linear regression equation | R |
|---|---|---|
| T1 | y = 89.0 x −116.7 | 0.9987 |
| T2 | y = 89.0 x −113.3 | 0.9997 |
| T3 | y = 92.0 x −116.3 | 0.9950 |
| T4 | y = 91.0 x −116.7 | 0.9961 |

Using these regression equations, the concentration of sodium in a sample can be determined from the measured EMF.

Example 4) Measurements of Native Human Urine Samples with Fabricated Sodium-Selective Test Strips and Comparison with the Results Obtained by Conventional Methods 17 different samples of native human urine (denoted with the numbers 1-17) were examined with the fabricated sodium sensor test strips. The samples were diluted 1:10 before measurement. As described above, each test strip was conditioned prior to measurement by immersion in a 1M NaCl solution. Afterwards, the test strip was dipped into the urine sample and the EMF measured by means of a potentiometer.

Using the linear regression equation, the concentrations of sodium in the urine samples (Table 3) were determined as illustrated by following example:

EMF of a sample measured with the T1 test strip: 27 mV

Regression equation: y=89.0x−116.7

−Log [Na+]=(27+116.7)/(−89.0)=−1.6146

[Na+]=$10^{-1.6146}$=0.0243

Because of 1:10 dilution prior to measurement multiplying by 10⇒0.243M=243 mM

TABLE 3

Overview of EMFs and corresponding Na concentrations obtained from measurements using four different test strips (T1 – T4) ant the corresponding regression equations in Tab. 2.

|  | EMF [mV] | | | | c(Na+) [mM] | | | |
| --- | --- | --- | --- | --- | --- | --- | --- | --- |
|  | T1 | T2 | T3 | T4 | T1 | T2 | T3 | T4 |
| 1 | 27 | 40 | 30 | 30 | 243 | 189 | 264 | 244 |
| 2 | 30 | 42 | 36 | 37 | 225 | 180 | 227 | 205 |
| 3 | 47 | 52 | 47 | 53 | 147 | 139 | 172 | 136 |
| 4 | 60 | 61 | 61 | 66 | 104 | 110 | 121 | 98 |
| 5 | 51 | 55 | 49 | 52 | 131 | 129 | 164 | 140 |
| 6 | 96 | 99 | 90 | 91 | 41 | 41 | 59 | 52 |
| 7 | 70 | 76 | 69 | 75 | 80 | 75 | 99 | 78 |
| 8 | 47 | 51 | 51 | 52 | 145 | 143 | 156 | 140 |
| 9 | 127 | 130 | 134 | 136 | 18 | 19 | 19 | 17 |
| 10 | 95 | 102 | 102 | 105 | 42 | 38 | 43 | 37 |
| 11 | 36 | 36 | 36 | 42 | 193 | 210 | 226 | 180 |
| 12 | 43 | 43 | 42 | 45 | 161 | 175 | 195 | 167 |
| 13 | 60 | 61 | 58 | 66 | 104 | 110 | 131 | 98 |
| 14 | 149 | 152 | 152 | 158 | 10 | 10 | 12 | 10 |
| 15 | 158 | 156 | 159 | 165 | 8 | 9 | 10 | 8 |
| 16 | 79 | 78 | 81 | 77 | 64 | 71 | 73 | 74 |
| 17 | 78 | 79 | 75 | 82 | 65 | 69 | 85 | 66 |

The same samples of human urine were analysed for their Na concentrations by conventional flame photometry (AAS) and classic Na-ISE (Table 4).

TABLE 4

Sodium concentrations (mM) in urines from 17 children measured by fabricated Na– selectivetest-strips according to this invention, classic Na-ISE and flame photometry (AAS).

|  | c(Na+) [mM] Test strip | c(Na+) [mM] classic Na-ISE | c(Na+) [mM] AAS |
| --- | --- | --- | --- |
| 1 | 221 | 215 | 188 |
| 2 | 197 | 188 | 158 |
| 3 | 140 | 131 | 99 |
| 4 | 101 | 74 | 71 |
| 5 | 132 | 136 | 112 |
| 6 | 44 | 16 | 50 |
| 7 | 77 | 46 | 55 |
| 8 | 138 | 130 | 166 |
| 9 | 17 | 8 | 12 |
| 10 | 38 | 21 | 41 |
| 11 | 193 | 177 | 171 |
| 12 | 166 | 169 | 162 |
| 13 | 105 | 103 | 92 |
| 14 | 10 | 7 | 10 |
| 15 | 9 | 6 | 11 |
| 16 | 68 | 52 | 70 |
| 17 | 70 | 60 | 97 |

Figure 6:
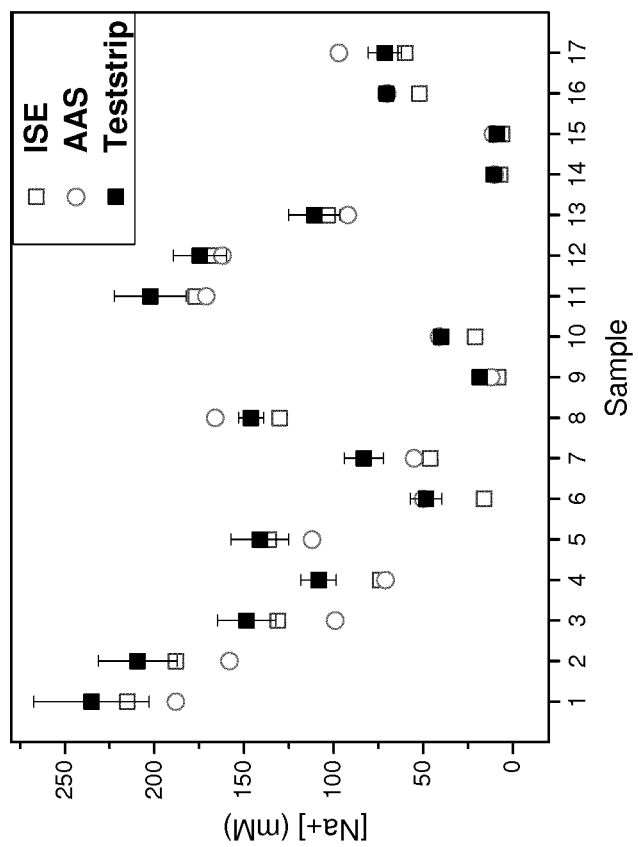
FIG. 6 shows a comparison of sodium concentrations determined by classic conventional sodium-iron-selective electrodes (ISE), by flame photometry (i.e. atomic absorption spectroscopy, AAS), which is the reference method of the International Federation of Clinical Chemistry (IFCC), and by an exemplary sodium-selective test-strip according to the present invention.

Sodium concentrations obtained by the four test-strip measurements were averaged and compared to the values determined by classic Na ISE and by flame photometry. As seen in FIG. 6 there is rather good agreement between the three methods. The differences between classic Na-ISE and flame photometry, both methods applied currently in clinical laboratories for sodium concentration determination, are in some cases even larger than between classic Na-ISE and the developed test strip.

Example 5) Fabrication of a Creatinine-Selective Test Strip

For proof-of-principle experiments, a commercially available 2-Electrode System (Gwent, UK, BE 2070921D1/007) was used. The system consists of a carbon working electrode (WE) with Ø=6 mm and a common (Ag/AgCl) counter/reference electrode (RE) that are both screen printed onto a 12.0×26.5 mm plastic substrate.

To realize a creatinine-selective electrode (Cr-SE), a selective membrane (Cr-SM) solution (30 µL) was casted on the area of the carbon WE. Then, the substrate was dried to remove solvent and form a selective membrane on the WE. The Cr-ISM solution consisted of a mixture of 1.8 mg Dibenzo-30-crown-10 (DB30C10), 1.8 mg potassium tetrakis (p-chlorophenyl)borate (PTp-ClPB), 65.5 mg o-nitrophenyl octyl ether (o-NPOE) and 30.9 mg PVC (high molecular weight polyvinylchloride) in 3 mL tetrahydrofurane.

Example 6) Potentiometric Measurements with a Creatinine-Selective Test Strip

Prior to measurement, for conditioning the Cr-selective electrode, the test strip was immersed overnight into a $10^{-2}$ M protonated creatinine aqueous solution. The substrate with both electrodes was introduced into the sample solution and the potential difference (EMF) between modified WE (Na-ISE) and RE was measured with a simple digital voltmeter.

Example 7) Sensor Calibration by Measuring a Standard Creatinine Solution Series Standard aqueous solutions of protonated creatinine with the concentration of 1M, $10^{-1}$M, $10^{-2}$M, and $10^{-3}$M respectively, were prepared. The EMF values were recorded and a calibration curve was set up by plotting the EMF values as a function of the minus logarithm of creatinine concentrations. Five different test strips (C1-C5) were fabricated and tested. The results are summarized in Table 5.

TABLE 5

EMF values for four different creatinine concentrations (1.0-0.001M) obtained by measurements with five different test strips (C1-C5)

| c[Cr] M | EMF [mV] C1 | EMF [mV] C2 | EMF [mV] C3 | EMF [mV] C4 | EMF [mV] Cr5 |
| --- | --- | --- | --- | --- | --- |
| $10^{-3}$ | −47 | −47 | −51 | −49 | −53 |
| $10^{-2}$ | −137 | −132 | −138 | −135 | −132 |

TABLE 5-continued

EMF values for four different creatinine
concentrations (1.0-0.001M) obtained by
measurements with five different test strips (C1-C5)

| c[Cr] M | EMF [mV] C1 | EMF [mV] C2 | EMF [mV] C3 | EMF [mV] C4 | EMF [mV] Cr5 |
|---|---|---|---|---|---|
| $10^{-1}$ | −223 | −212 | −220 | −213 | −212 |
| $10^{0}$ | −306 | −301 | −307 | −305 | −301 |

Figure 7:
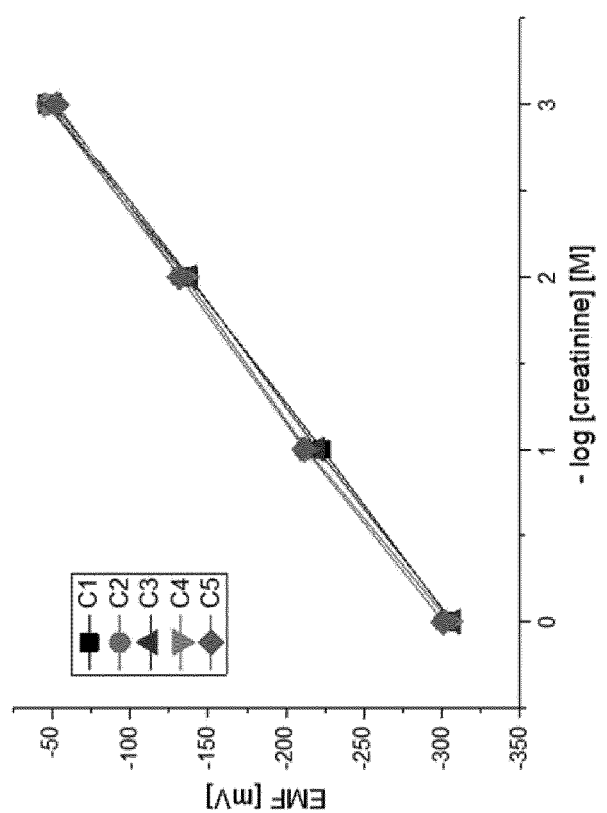
FIG. 7 shows a potentiometric response of exemplary fabricated test-strips in accordance with the present invention (C1-C5) to different creatinine concentrations in aqueous solutions.

The data clearly show good reproducibility and—as shown in FIG. 7—a linear (dynamic) range between 0.001 and 1 M creatinine solution. Thus, the linear range of the test strips covers medically relevant concentrations in physiological fluids, as in urine with values of 0.004-0.02 M.

Out of these data for each test strip, a regression equation, listed in Table 6 with the correlation coefficient R, was calculated.

TABLE 6

Overview of linear regression equations and
correlation coefficients obtained from EMF measurements
with five different creatinine sensors (C1-C5)

| Test strip | Linear regression equation | R |
|---|---|---|
| C1 | y = 86.3 x −307.7 | 0.9995 |
| C2 | y = 84.2 x −299.3 | 0.9994 |
| C3 | y = 85.0 x −306.5 | 0.9998 |
| C4 | y = 84.6 x −302.4 | 0.9986 |
| C5 | y = 82.4 x −298.1 | 0.9988 |

Example 8) Sensor Calibration with Stabilized Reference Electrode Potential Showing Near-Nernst Response in a Biologically Relevant Range The potential of the Ag/AgCl counter/reference electrode (RE) on the used commercial test-strip (Gwent, UK, BE 2070921D1/007) depends on the chloride ions concentration in the sample. To achieve a stable reference electrode potential, a saturating concentration of chloride ions are added to the standard solutions from which the sensor is calibrated.

Therefore, sodium standard solutions with concentrations of 1M, $10^{-1}$M, $10^{-2}$M, $10^{-3}$M, respectively, were prepared by dissolving sodium chloride (NaCl) in a 0.5 M calcium chloride ($CaCl_2$) aqueous solution. The sodium sensor was fabricated as described in Example 1 and the EMF values were recorded as described in Example 2. A calibration curve was set up by plotting the EMF values as a function of the minus logarithm of sodium concentrations. Three different test strips (T5-T7) were fabricated and tested. The results are summarized in Table 1.

TABLE 7

EMF values for four different Na concentrations (1.0-0.001M)
obtained by measurements with three different test strips (T5-T7)

| c(Na+) [M] | EMK [mV] T5 | EMK [mV] T6 | EMK [mV] T7 |
|---|---|---|---|
| 1 | 324 | 320 | 332 |
| 0.1 | 272 | 270 | 275 |
| 0.01 | 217 | 216 | 223 |
| 0.001 | 157 | 158 | 161 |

Out of these data for each test strip a regression equation with the corresponding correlation coefficient R, was calculated (Table 8).

TABLE 8

Overview of linear regression equations and
correlation coefficients obtained for EMF
measurements with three different sodium sensors (T5-T7)

| Sensor | Linear regression equation | R |
|---|---|---|
| T5 | y = −55.6 x +325.9 | 0.9984 |
| T6 | y = −54.0 x +322.0 | 0.9983 |
| T7 | y = −56.5 x +332.5 | 0.9984 |

REFERENCES

1. Upadhyay A, Jaber B L, Madias N E. Incidence and prevalence of hyponatremia. Am J Med 1; S30-S35 (2006)
2. Moritz M L, Ayus J C. Maintenance intravenous fluids in acutely ill patients. N Engl J Med 373; 1350-60 (2015)
3. Moritz M L, Ayus J C. Disorders of water metabolism in children: hyponatremia and hypernatremia. Pediatr Rev 23; 371-380 (2002)
4. Blank M C. Bedarf J R, Russ M, Grosch-Ott S, Thiele S, Unger J K. Total body Na(+)-depletion without hyponatremia can trigger overtraining-like symptoms with sleeping disorders and increasing blood pressure: explorative case and literature study. Med Hypotheses 79; 799-804 (2012)
5. Heinz-Erian P, Akdar Z, Haerter B, Waldegger S, Giner T, Scholl-Buergi S, Müller T. Decreased urinary-sodium-to-creatinine ratio identifies sodium depletion in pediatric acute gastroenteritis. Klin Padiatr 228; 24-8 (2016)
6. Coates A J, Crofton P M, Marshall T. Evaluation of salt supplementation in CF infants. J Cyst Fibr 8; 382-5 (2009)
7. Knepper C, Ellemunter H, Eder J, Niedermayr K, Haerter B, Hofer P, Scholl-Bürgi S, Müller T, Heinz-Erian P. Low sodium status in cystic fibrosis—as assessed by calculating fractional Na+ excretion—is associated with decreased growth parameters. J Cyst Fibr 15; 400-5 (2016)
8. Sahay M, Sahay R. Hyponatremia: a practical approach. Indian J Endocrinol Metab 18; 760-771(2014)
9. Wassner S J, Kulin H E. Diminished linear growth associated with chronic salt depletion. Clin Pediatr; 29; 719-21 (1990)
10. Rodriguez M J, Alcaraz A, Solana M J et al. Neurological symptoms in hospitalized patients: do we assess hyponatremia with sufficient care? Acta Paediatr 103; e7-e10 (2014)
11. Corona G, Guiliani C, Parenti G et al. Moderate hyponatremia is associated with increased risk of mortality: evidence from a meta-analysis. PLOS ONE 8; e80451 (2013)
12. Moritz M L, Ayus J C. New aspects in the pathogenesis, prevention and treatment of hyponatremic encephalopathy in children. Pediatr Nephrol 25; 1225-38 (2010)
13. Thomas L. Messung von Natrium. In: *Labor and Diagnose*. TH-Books 5. Auflage, Kap. 8.2, pp 295-303
14. Maas A H. IFCC reference methods for measurement of pH, gases and electrolytes in blood: reference materials, Eur J Clin Chem Clin Biochem 29; 253-261 (1991)

15. Randvir E P, Banks C E. Analytical methods for quantifying creatinine within biological media. Sensors & Actuators B 183; 239-52 (2013)
16. Vashist S K, Luppa P B, Yeo L Y, Ozcan A, Luong J H T, Emerging Technologies for Next-Generation Point-of-Care Testing. Trends in Biotechnology, 33, 11; 692-705 (2015)
17. Yetisen A K, Akram M S, Lowe C R. Paper-based microfluidic point-of-care diagnostic devices, Lab Chip 13; 2210-52 (2013)
18. Weber J A., Zanten van A P. Interferences in current methods for measurements of creatinine. Clin. Chem. 37/5; 695-700 (1991)
19. Syal K., Banerjee D., Srinivasan A. Creatinine estimation and interference. Ind J Clin Biochem 28(2); 210-211 (2013)
20. C. S. Pundir C S. Sandeep Yadav S. Kumar A. Creatinine sensors, TRAC 50; 2-52 (2013)
21. https://www.pointofcare.abbott/int/en/offerings/istat/istat-handheld
22. Shephard M D S, Point-of-Care Testing and Creatinine Measurement, Clin Biochem Rev, 32; 109-114 (2011)
23. Yafia M, Shukla S, Najjaran H, Fabrication of digital microfluidic deviceson flexible paper-based and rigid substrates via screen printing, J. Micromech. Microeng. 25; 1-11 (2015)
24. Whitesides G M. Electrochemical sensing in paper-based microfluidic devices. Lab Chip 10; 477-483 (2010)
25. Schrier R W. Diagnostic value of urinary sodium, chloride, urea and flow. J Am Soc Nephrol 22; 1610-1613 (2011)
26. Espinel C H. The FENa test. Use in the differential diagnosis of acute renal failure. JAMA 236; 579-581 (1976)
27. Winkler S S, Thomasson D M, Sherwood K, Perman W H. Regional T2 and sodium concentration estimates in the normal human brain by sodium-23 MR imaging at 1.5 T. J Comput Assist Tomogr 13; 561-5 (1989)

The features disclosed in the foregoing description, in the claims and/or in the accompanying drawings may, both separately and in any combination thereof, be material for realizing the invention in diverse forms thereof.

The invention claimed is:

1. A single-use test-strip for the quantitative determination of sodium concentration and creatinine concentration in a patient's urine sample, said test-strip comprising:
    a substrate which either is electrically insulating or which has an electrically insulating layer applied thereon,
    an electrode assembly applied on said substrate or on said electrically insulating layer, if present,
    said electrode assembly comprising at least
        one sodium-selective working electrode;
        one creatinine-selective working electrode;
        either one joint reference electrode for both said sodium-selective working electrode and said creatinine-selective working electrode, or a reference electrode for said sodium-selective working electrode and a separate reference electrode for said creatinine-selective working electrode;
        one or two neutral electrodes for measuring and eliminating interferences, wherein the one or two neutral electrodes comprise a membrane comprising a polymeric matrix without any sodium-selective carrier and without any creatinine-selective carrier; and
    an interface for electrically connecting said electrode assembly to a readout-meter device.

2. The single-use test-strip according to claim 1, wherein said working electrodes, said reference electrode(s) and said neutral electrode(s) have been applied on said substrate or on said electrically insulating layer, if present, by a suitable deposition technique, selected from printing, sputtering, evaporating, electro-less plating, affixation, gluing and lithography, thus forming an electrode assembly on said substrate or on said electrically insulating layer, and wherein said sodium-selective working electrode comprises a sodium-selective membrane, and said creatinine-selective working electrode comprises a creatinine-selective membrane, and wherein said neutral electrode(s) comprises (comprise) a membrane that is not sodium-selective and not creatinine-selective.

3. The single-use test-strip according to claim 1, wherein said substrate is made of a material selected from plastic, ceramic, alumina, paper, cardboard, rubber, textile, carbon-based polymers, fluoropolymers, silicon-based substrates, silicon based polymers, semiconducting materials, dielectric materials, inorganic dielectric materials, and wherein said electrically insulating layer, if present, is made of a dielectric material, wherein, if said electrically insulating layer is present on said substrate, said electrode assembly is located on said electrically insulating layer.

4. The single-use test-strip according to claim 2, wherein said sodium-selective working electrode comprises a sodium-selective membrane that comprises a sodium-selective carrier in a polymer matrix, and said creatinine-selective membrane comprises a creatinine-selective carrier in a polymer matrix.

5. The single-use test-strip according to claim 1, wherein each of said electrodes in said electrode assembly has an electrical lead, respectively, wherein said electrical lead connects said electrode with said interface for electrically connecting said electrode assembly to a readout-meter device.

6. The single-use test-strip according to claim 1, wherein said joint reference electrode has a surface larger than the surface of each of said working electrodes, or each of said separate reference electrodes has a surface larger than the surface of each of said working electrodes.

7. A non-invasive point-of-care (POC) device for detecting sodium depletion and/or sodium overload in a patient's body, said POC device comprising:
    a readout-meter device for the quantitative and selective measurement of sodium and creatinine concentrations in a urine sample and for determining a ratio of sodium-to-creatinine, said readout-meter device comprising
        a receiving module for receiving an interface of a single-use test-strip according to claim 1 and for establishing electrical contact between said readout-meter device and an electrode assembly of said single-use test-strip, thus allowing the detection and transmission of electrical signal(s) from said single-use test-strip to said readout-meter device, wherein said receiving module has electrical connectors for separately contacting each electrode via said interface of said test-strip
        a multichannel amplifier, having high input resistance, for amplifying electrical signal(s) transmitted from said single-use test-strip
        a controller including an analog/digital converter and a storage memory, for converting electrical signals received from said single-use test-strip into sodium concentration measurement(s) and creatinine concentration measurement(s) and for subsequently determining a ratio of sodium concentration to creatinine concentration based on said sodium concentration measurements and creatinine concentration measurements an output device for indicating concentration measurements and/or said ratio to a user, and a power supply.

8. The non-invasive point-of-care (POC) device according to claim 7, wherein said single-use test-strip is inserted into said receiving module of said readout-meter-device by way of said interface of said single-use test-strip, thus establishing electrical contact between said electrode assembly of said test-strip and said readout-meter device.

9. The non-invasive point-of-care (POC) device according to claim 7, wherein said device further comprises:

a user-interface for operating said device, and/or a memory for storing a plurality of sodium and creatinine concentration measurements and calculated ratios of sodium concentration to creatinine concentration, and/or a connection interface, for transferring and/or exchanging data with an external computer or external network.

10. A method for quantitatively determining sodium concentration and creatinine concentration in a patient's urine sample, comprising the steps:

a) providing a urine sample b) contacting a single-use test-strip according to claim 1 with said urine sample and allowing the electrode assembly of said test-strip to be wetted by and come into contact with said urine sample, optionally withdrawing the urine-wetted test-strip from said urine sample c) connecting said test-strip to a readout-meter device of a point-of-care (POC) device for detecting sodium depletion and/or sodium overload in a patient's body, said POC device comprising:

a readout-meter device for the quantitative and selective measurement of sodium and creatinine concentrations in a urine sample and for determining a ratio of sodium-to-creatinine, said readout-meter device comprising a receiving module for receiving an interface of a single-use test-strip according to claim 1 and for establishing electrical contact between said readout-meter device and an electrode assembly of said single-use test-strip, thus allowing the detection and transmission of electrical signal(s) from said single-use test-strip to said readout-meter device, wherein said receiving module has electrical connectors for separately contacting each electrode via said interface of said test-strip a multichannel amplifier, having high input resistance, for amplifying electrical signal(s) transmitted from said single-use test-strip a controller including an analog/digital converter and a storage memory, for converting electrical signals received from said single-use test-strip into sodium concentration measurement(s) and creatinine concentration measurement(s) and for subsequently determining a ratio of sodium concentration to creatinine concentration based on said sodium concentration measurements and creatinine concentration measurements an output device for indicating concentration measurements and/or said ratio to a user, and a power supply, wherein said single-use test-strip is inserted into said receiving module of said readout-meter device, thus establishing electrical contact between said electrode assembly of said test-strip and said readout-meter device, wherein said connecting of said test strip to said readout-meter device of said POC device in step c) occurs either before or after step b), d) measuring sodium concentration and creatinine concentration in said urine sample, using said POC device assembled in step c).

11. A method of detecting sodium depletion and/or sodium overload in a patient's body, said method comprising the steps:

performing the method according to claim 10 determining a ratio of sodium concentration to creatinine concentration using said point-of-care (POC) device detecting a sodium depletion, if a calculated ratio of sodium concentration to creatinine concentration in said urine sample is <8, and detecting a sodium overload, if a calculated ratio of sodium concentration to creatinine concentration is >50.

12. The method according to claim 11, wherein said sodium depletion is a sodium depletion in the plasma of a patient, or is a normonatremic sodium depletion, wherein, in such normonatremic sodium depletion, the sodium concentration in the plasma of a patient is in a normal healthy range, but the patient suffers from a depleted total body sodium pool.

13. The single-use test-strip, according to claim 2, wherein said deposition technique is screen printing or ink jet printing.

14. The single-use test-strip according to claim 3, wherein said substrate is made of a material selected from polypropylene, Teflon, glass, quartz, silicon nitride, silicon oxide, polydimethoxysiloxane, elemental silicon, polyimide, polycarbonate, polyvinyl chloride, polystyrene, polyethylene, polypropylene, polyester, polyethylene terephthalate, polyurethane, polyvinylidene fluoride, and silicium dioxide.

* * * * *